United States Patent [19]

Holtkamp, Sr.

[11] Plant 4,376

[45] Feb. 6, 1979

[54] ANTHURIUM PLANT

[76] Inventor: Hermann Holtkamp, Sr., Kueningsmuehle, 2 Dingden, 4236 Hamminkeln, Fed. Rep. of Germany

[21] Appl. No.: 920,226

[22] Filed: Jun. 28, 1978

[51] Int. Cl.[2] ..... A01H 5/00

[52] U.S. Cl. ..... Plt./88

[58] Field of Search ..... Plt./88

*Primary Examiner*—Robert E. Bagwill
*Assistant Examiner*—James R. Feyrer
*Attorney, Agent, or Firm*—Donald D. Jeffery

[57] ABSTRACT

The new anthurium cultivar Senior I is characterized by its fast and compact growth habit; orange-red, generally heart shaped spathe having a grooved or ridged surface and a slight indentation along one side thereof; early blooming habit; straight and strong petioles, light to medium green leaves which provide an attractive contrast with the orange-red spathe and white-yellow spadix; propagation by side shoots or tissue culture, and by its suitability for pot production.

1 Drawing Figure

The present invention comprises a new and distinct cultivar of anthurium, botanically known as *Anthurium andraeanum,* and hereinafter referred to by the cultivar name Senior I.

The new cultivar is a product of a planned breeding program, and is generally characterized by its orange-red and heart shaped spathe, with one edge thereof being uniquely indented; straight and strong petioles; white-yellow spadix, very compact growth habit, and by the spathe appearing just above the leaves.

The new cultivar was originated from a cross made by me in a controlled breeding program in Isselburg, Rhineland, Germany. The female, or seed parent was GUATMALA 96, and the male, or pollen parent was GUATMALA 31. The new cultivar Senior I was discovered and selected as a flowering plant within the progeny of the stated cross by me in a controlled environment in Isselburg, Rhineland, Germany. Asexual reproduction of the new cultivar is possible by tissue culture or by side shoots, and asexual reproduction has demonstrated that the combination of characteristics as herein disclosed for the new cultivar are firmly fixed and are retained through successive generations.

The following observations, measurements and values describe plants grown in Isselburg under greenhouse conditions which closely approximate those generally used in horticultural practice.

The following traits have been repeatedly observed and have been determined to be characteristics which in combination distinguish Senior I from other anthuriums of the same general type:

1. Orange-red spathe, small to medium size, 75–150 mm. in diameter.
2. Compact growth habit, being approximately 35 cm. tall when grown to maturity in an 11 cm. pot.
3. Light to medium green leaves, underside being lighter; young leaves are brown.
4. Petioles are wiry and light green in color.
5. Spadix approximately 35 mm. long and 6–9 mm. in diameter; yellow at a young stage of growth, and ivory-white when mature.
6. The main plant produces several off-shoots at the base of the stem.
7. Very early bloom, approximately 9–12 months after being cultivated in an 11–12 cm. pot.

The accompanying photographic drawing shows a typical specimen of the new cultivar, with the colors appearing in the photograph being as true as possible with color illustrations of this type.

In the following description, color references are made to the Royal Horticultural Society (RHS) Color Chart, 1966 edition, except where general color terms of ordinary significance are obvious.

Botanical classification: *Anthurium andraeanum,* cultivar name, Senior I.

Parentage:

*Male parent.*—*Anthurium andraeanum* GUATMALA 31.

*Female parent.*—*Anthurium andraeanum* GUATMALA 96.

Propagation: Propagation through tissue culture or by side shoots has established that the new cultivar holds its distinguishing characteristics from generation to generation.

Plant: When grown in an 11 cm. pot, the plant when mature is 30–40 cm. tall and approximately 30 cm. in diameter.

Leaves:

*Form and size.*—The leaves are generally heart shaped, with a distinct point. The diameter, depending on the size of the plant, is approximately 80 × 120 mm. up to 120 × 180 mm., and larger. The leaves when fully grown are of equal size and shape, and somewhat curled up at the edges.

*Texture.*—Leathery and very smooth, slightly shiny.

*Veins.*—Very visible and well-developed, particularly standing out on the underside of the leaves.

*Color.*—The color of a young leaf on the upperside is RHS 138 A, for older leaves 137 A. On the underside, the color is also 137 A. The petiole is very straight and wiry, and light green in color.

Flowers:

*Buds.*—The spathe is rolled around the spadix and is shaped and pointed like a cigar; after opening, the spathe stands above the leaves. The bud stands horizontally on the pedicle. The open spathe stands slightly bent forward.

Spathe (blossom):

*Size.*—Approximately 80 × 150 mm.

*Color.*—Upperside, 40 A-B. Underside, 40 C-D.

*Arrangement.*—Spathe stand on straight, wiry pedicles, and are slightly bent forward at an angle of approximately 45° to the pedicle. The spathe are positioned slightly above the leaves.

*Shape.*—At full bloom, the spathe is of a roundish, heart shape. Its veins are very visible. The spathe is not smooth, but rather irregular and grooved on the upperside and underside. The edge of the spathe is indented on one side, a unique and distinguishing characteristic.

*Flowering time.*—After 8–10 months of being potted in an 11 cm. pot, the plant will be in bloom with 3–5 blossoms and buds. Small blossoms are seen somewhat earlier.

Reproductive organs: Spadix approximately 30–40 mm. long and 7–9 mm. in diameter. At an early stage, when the pistil and stamens are not yet mature, the spadix is yellow, later becoming white.

*Stamens.*—Around the pistil are four stamens. They are visible only when separating the individual reproductive organs from the pulpy main axle. The stamens are covered with 2 small triangular and 2 square shaped tops; at the center, the stamen is firmly enclosed.

*Anthers and filaments.*—Not clearly visible.

*Pollen.*—White-yellow in color.

*Pistils.*—Firmly grown together with the pulpy main axle and sitting between the stamens. The style is yellow-white and shaped slightly square, approximately 3–5 mm. long.

Roots: Very pulpy and light yellow-brown; tips of roots white, well branched out; when exposed to light, the roots become light-green.

Disease Resistance: Through experiences to date, very good against traditional diseases.

General observations:

Senior I is a very fast growing *Anthurium andraeanum,* and is very compact and bushy. At an early stage of growth, the plant gets into bloom with small blossoms or spathe which become bigger with the growth of the plant. The new cultivar is suited especially as a potting plant, as contrasted to the normal *Anthurium andraeanum,* which is cultivated as a cut flower. Senior I, with the combination of characteristics described above, is a unique new cultivar.

I claim:

1. A new and distinct cultivary of anthurium, substantially as described and illustrated, known by the cultivar name Senior I and particularly characterized by the combined features of fast and compact growth habit; orange-red, generally heart shaped spathe having a grooved or ridged surface and a slight indentation along one side thereof; early blooming habit, straight and strong petioles, light to medium green leaves which provide an attractive contrast with the orange-red spathe and white-yellow spadix; propagation by side shoots or tissue culture, and by its suitability for pot production.

* * * * *

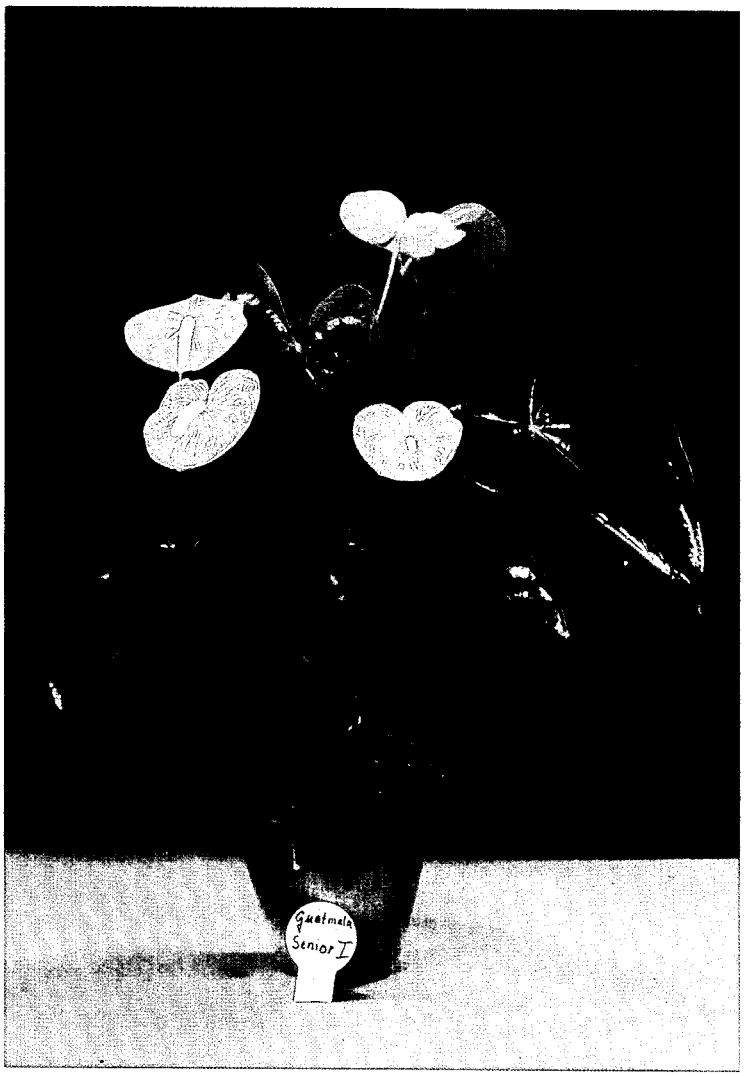
Guatmala
Senior I